US006465640B1

(12) United States Patent
Hood

(10) Patent No.: US 6,465,640 B1
(45) Date of Patent: Oct. 15, 2002

(54) METHOD AND DEVICE FOR PURIFYING NUCLEIC ACIDS

(75) Inventor: Robert Gordon Hood, Longforgan (GB)

(73) Assignee: FSM Technologies Limited, Glasgow (GB)

( * ) Notice: Subject to any disclaimer, the term of this patent is extended or adjusted under 35 U.S.C. 154(b) by 0 days.

(21) Appl. No.: 09/700,403

(22) PCT Filed: May 13, 1999

(86) PCT No.: PCT/GB99/01528

§ 371 (c)(1),
(2), (4) Date: Apr. 5, 2001

(87) PCT Pub. No.: WO99/60005

PCT Pub. Date: Nov. 25, 1999

(30) Foreign Application Priority Data

May 15, 1998 (GB) .............................................. 9810403

(51) Int. Cl.[7] .......................... C07H 21/00; C07H 21/02; C07H 21/04; C12N 1/08

(52) U.S. Cl. ..................... 536/25.4; 536/25.41; 435/270

(58) Field of Search .............................. 536/25.4, 25.41, 536/28, 29; 435/270

(56) References Cited

U.S. PATENT DOCUMENTS 5,438,128 A    8/1995   Nieuwkerk et al.

FOREIGN PATENT DOCUMENTS

| WO | WO95/02049 | 1/1995 |
| WO | WO96/04067 | 2/1996 |
| WO | WO96/17673 | 6/1996 |

Primary Examiner—Remy Yucel
Assistant Examiner—Konstantina Katcheves
(74) Attorney, Agent, or Firm—Wallenstein & Wagner, Ltd.

(57) ABSTRACT

The present invention concerns methods for purifying nucleic acids from whole cells in a sample, such as whole blood. Also provided is the use of a filter device in same.

16 Claims, 3 Drawing Sheets

METHOD AND DEVICE FOR PURIFYING NUCLEIC ACIDS

The present invention concerns the separation of nucleic acids from whole cells in a sample. In particular, it concerns the recovery of genomic DNA from cells of a patient blood sample.

Current techniques of separating nucleic acids from a sample can be both time consuming and costly, involving separate steps of cell lysis, nuclei lysis, protein precipitation, DNA rehydration and RNA digestion. One of the many kits available for genomic DNA purifiction from e.g. whole blood samples is the Wizard (RTM) Genomic DNA Purification Kit supplied by Promega Kit sufficient to purify 50×3 ml of sample can be very expensive and performing the protocol takes about 45 minutes. Other techniques are available but typically take longer to perform and require the use of proteinases or organic solvents, or the use of columns or resins to purify fractions of a sample.

The present invention improves upon the prior art, providing a novel method for purifying nucleic acids from whole cells in a sample. According to the present invention there is provided a method for purifying nucleic acids from whole cells in a sample comprising passing the sample across the surface of at least one porous membrane contained in a filter device having a sample inlet and a sample outlet, the path from the inlet to the outlet being partially occluded by the membrane or membranes and generating a transmembrane pressure.

The technique of filtering flow across the surface of a membrane is widely known as "cross-flow filtration" (see for example Hood, R, 1998, New Frontiers in Screening for Microbial Biocatalysts, 77–86; WO 96/04067; WO 96/04068; WO 96/17673; WO96/20402). Other membrane devices include those of U.S. Pat. No. 5,438,128. However, none of them provide for flow around the membranes (as opposed to through it or across it by only partially occluding the path between sample inlet and outlet). The present inventor has found that, surprisingly, this can be used to rupture cellular and nuclear membranes to purify nucleic acids. By only partially occluding the path between the inlet and the outlet, i.e. by providing for flow around the membrane or membranes, it is possible for larger pieces of cellular debiris to pass around the membrane rather than clogging the pores. Not only are the cells ruptured, but the nucleic acids contained in the cell are deposited upon the surface and interior of the membrane. Experiments (below) have shown that a very substantial proportion of cellular nucleic acids are retained by the membrane. Furthermore, tests (see below) using molecular weight markers as standards for comparison have also shown that the average molecular weight of recovered DNA is very high, indicating that although the shearing forces exerted upon the cells are sufficient to rupture cellular and nuclear membranes, they are not so great as to cause extensive shearing of nucleic acids.

This is particularly important for subsequent testing of recovered nucleic acids since damaged strands may not display an appropriate binding site (e.g. epitope) or may not provide a sequence sufficient for correct PCR primer binding and elongation in order to effect amplification.

A minimum transmembrane pressure of 0.25 bar is required to effect cellular rupturing. As the transmembrane pressure is increased, rupturing is more efficient, there is a slight increase in shearing of nucleic acids and, at higher pressures, membrane deformation can occur. As the transmembrane pressure is increased it is also found that more of the nucleic acids are deposited in the pores/interstices of the filter membrane, and at high transmembrane pressures it is possible that nucleic acids, particularly shorter stretches of nucleic acids, may be forced through the membrane altogether and thus not be retained on the membrane. Due to all of this, a maximum transmembrane pressure of about 1.25 bar appears to be appropriate, although of course the maximum transmembrane pressure for a particular device may be readily determined using simple experiments.

Light-microscope examination of membranes has shown their surface to be covered in nucleic acids and no other cellular components to be visible.

Removal of other cellular components may be further improved when using membranes having a lumen (e.g. hollow fibre membranes) by allowing the exit of filtrate via the lumen. For example, one end of a hollow fibre membrane (or series of hollow fibre membranes) may be sealed and the other end of the membrane(s) connected to a lumen restrictor valve to allow escape of filtrate when it is at a sufficiently high pressure to open the restrictor valve. For example, a device having a 0.5 bar outlet valve restrictor may be used with a lumen outlet having a 0.25 bar restrictor valve. Alternatively, the pressure required to open the lumen restrictor valve may be greater than that for the outlet valve, in which case nucleic acids will be more predominantly deposited on the outside of the membrane rather than in the pores/interstices. Too low a pressure required to open the lumen restrictor may result in too high a transmembrane pressure, in turn resulting in increased nucleic acid shearing and loss of nucleic acids through the lumen outlet. Appropriate values for outlet and lument restrictor valves may be readily determined by one skilled in the art using simple experimentation.

Experiments (below) have also shown that successful PCR amplification may be performed directly on the membranes carrying bound nucleic acids—RNA may be amplified using an initial step of reverse transcription. PCR techniques are well known (PCR (Volume 1): A practical approach. Eds. M. J. McPherson, P. Quirke and G. R. Taylor. Oxford University Press, 1991) and may be readily used.

The simple methodology of the present invention means that the apparatus used may be relatively inexpensive. Importantly, nucleic acids, particularly genomic DNA, may be recovered from a sample such as a whole blood sample in a very short length of time—experiments (below) show that nucleic acids may be separated from 5×1 ml samples in a total of about 2 minutes.

Naturally, it is desirable to recover the greatest possible quantity of nucleic acids from a sample and so the membrane or membranes may occlude most of the path between the inlet and outlet. For example, the membrane may occupy at least 90% of the cross-sectional area of the filter device between the inlet and the outlet. In this way maximum cellular contact with the membrane (and thus cellular rupturing and nucleic acid recovery) is achieved whilst allowing flow of cellular debris around the membrane, thus ensuring that the final membrane-bound nucleic acids are substantially free of impurities. It may also be desirable to prefill the filter device with e.g. an appropriate buffer prior to introducing the sample so that pressure is exerted upon the whole of the sample as it passes from inlet to outlet. Similarly, a flush step may be used after the sample has been introduced into the filter device in order to ensure that it all (except for that retained by the membrane) passes through to the outlet.

The pores in the membrane act to allow the creation of a transmembrane pressure difference and allow the trapping of nucleic acids. The pores also allow smaller pieces of cellular debris to easily pass through to the outlet. Pores may have a molecular weight cut off (MWCO) of $10^5$–$10^7$ daltons, for example, about $10^6$ daltons.

Examples of membranes which may be used are a polypropylene membrane with a pore diameter of 0.2 μm (for example supplied by AKZO NOBEL) and polysulphone membranes models ULF 1 million and ULF 750 supplied by A/G Technologies Corp. USA, as well as models 9002 and 9005 supplied by Fresenius A. G. (St. Wendel, Germany). The membranes should not repel the nucleic acids and so it may be necessary to pre-treat them to ensure they are hydrophilic and/or have a positive charge. In the case of polypropylene membranes, they may be pre-soaked in a solution of 20% Tween. Membranes having coarse surfaces may be used in order to enhance the rupturing of cellular and nuclear membranes. This may if necessary be achieved by pretreatment of the membranes.

Various types of membrane may be used, for example flat (sheet) membranes and hollow fibre membranes.

The membranes may be treated with agents which detect particular nucleic acids or nucleic acid sequences. For example, a membrane may be pre-treated with antibody specific against an RNA sequence. Binding of RNA to the antibody may be subsequently detected by a change in the absorption/fluorescence by the antibody. Antibodies, their manufacture and uses are well known (Harlow, E. and Lane, D., "Antibodies—A Laboratory Manual", Cold Spring Harbor Laboratory, Cold Spring Harbor Press, New York, 1988). Alternatively, an ELISA-style test may be performed. Alternatively, a first antibody may be applied to nucleic acids purified on the membrane. After washing to remove non-specifically bound antibody, a second antibody specific against the first may be applied, the second antibody having conjugated to it a signalling molecule such as luciferase, thus providing an amplified detection signal. A capture probe may be used with polymerase DNA which serves as a capture probe for target or complementary DNA sequences within the device on immobilised DNA on the surface of the membrane (for example, Mosaic Technologies Inc. Acrydite DNA Gel).

In the case of hollow fibre membranes it is possible to pass a reagent or series of reagents along the volume of the fibre. Thes reagents may detect e.g. specific DNA or RNA sequences. The reagents may be chosen in combination with the membrane in order that they do not exit the membrane as they pass along it, thus ensuring that only materials (i.e. nucleic acids) bound to the membrane are contacted by the reagents.

Also provided according to the present invention is a filter device having a sample inlet and a sample outlet, the path from the inlet to the outlet being partially occluded by at least one porous membrane, the device when in use providing a transmembrane pressure of at least 0.25 bar. The filter device may be for use in a method for purifying nucleic acids. The filter device may be used in a method of purification of nucleic acids according to the present invention.

Typical filter devices used according to the present invention comprise an inlet and an outlet (made from PVC) with an internal diameter of 1.25 mm, the outlet being fitted with a 0.5 bar restrictor valve. The inlet and outlet are arranged perpendicular to the main body of the filter device and on opposite sides of it. The total length of the main body (3.25 mm internal diameter) is 60 mm with the inlet and outlet being 30 mm apart. 14 fibres of polysulphone membrane type ULF 750 or 1 million, or 9002 (Fresenius A. G., St. Wendel, Germany) are provided along the length of the main body and have a total surface area of 6.28 cm$^2$.

An alternative device has the same physical dimensions as above but is provided with 6 fibres of a polysulphone membrane type ULF 750 or 1 million or 9005 (Fresenius A. G.) along the length of the main body, giving a total membrane surface area of 6.28 cm$^2$.

An alternative device has the same physical dimensions as above but is provided along the length of the main body with 4 polypropylene fibres having a pore size of 0.2 μm, giving a total membrane surface area of 6.28 cm$^2$.

Membranes having a larger pore size (e.g. ULF 1 million) are useful for purifying nucleic acids having a longer average length when compared to membranes having a smaller pore size (e.g. ULF 750). This appears to be due to sample turbidity turbid samples (for example blood which has undergone partial clotting) require more force to pass them through the device of the present invention than do less turbid samples (e.g. fresh blood). The more force that is required, the more mechanical damage occurs to the nucleic acids being purified, and thus the shorter the average length of the purified nucleic acids. Similarly, providing a membrane having a small pore size means that more force is required to remove from the membrane the non-nucleic acid parts of the sample being purified, and thus more mechanical damage occurs and shorter nucleic acid fragments are purified.

As discussed above, where hollow fibre membranes are used, additional lumen outlets may be provided to remove filtrate collected in the lumens of the filter membranes.

Also provided according to the present invention is the use of a filter device according to the present invention in a method of purification of nucleic acids according to the present invention.

Once the nucleic acids have been captured on a membrane using the method of the present invention, they may not only be analysed and e.g. sequenced as detailed above, but may also be eluted from the membrane. In order to achieve this an electrical current may be applied to a solution surrounding the membrane. For example, a DC current of 0.2 amps at 1000 volts may be applied, causing the nucleic acids captured on the membrane to dissociate from it. Once in solution the nucleic acids may be further processed. The exact nature of the electrical current applied to the captured nucleic acids may of course vary from the example given above, and appropriate conditions will be readily apparent to one skilled in the art. For example, it has been found there is an inversely proportional relationship between the average size of nucleic acid molecules to eluted and the voltage which needs to be applied in order to elute them, i.e. shorter nucleic acid molecules require greater voltages to be applied than longer nucleic acid molecules. Without wishing to be restricted by a particular reasoning for this, it does appear that longer nucleic acid molecules have fewer points of contact with the membrane per unit length than shorter nucleic acid molecules and therefore require less electrical current in order to be separated from the membrane.

The ability to elute nucleic acids from the membrane once they have been separated from whole cells in a sample means that nucleic acids may be purified from a large volume of e.g. whole blood and then eluted into a relatively small volume of fluid, making subsequent analysis simpler and easier.

Because the different nucleic acid molecules have different physical characteristics, when eluting nucleic acids, different nucleic acids (e.g. bacterial DNA and human genomic DNA) may be separated from one another by using an appropriate electrical current (i.e. by performing electrophoresis), e.g. by using an AC current, optionally varying its frequency (see "Shock Treatment", New Scientist, Jun. 6, 1998; "Devilish tricks with tiny chips", New Scientist, Mar. 1, 1997, p. 22; and references therein).

The AC current may have a frequency of between 100 hertz and 10 megahertz. For example, a 100 kilohertz current applied along the length of the membrane will cause bacterial and human genomic DNA to move relative to one another.

The methods and devices of the present invention may be used in conjunction with gene chip technology—once nucleic acids have been purified by collection on the surface of the membrane, is may be contacted with a gene chip, the gene chip being subsequently analysed to determine the presence or absence of specific nucleic acids in the purified nucleic acids.

Alternatively, a gene chip may be provided on the surface of the porous membrane or membranes. After purification has occurred, non-hybridised nucleic acids may be removed and the gene chip analysed.

This use of gene chip technology can provide for an extremely rapid analysis of a sample containing whole cells, allowing for the collection purification and analysis of nucleic acids from the cells in a single device and in an extremely short period of time.

In order to improve the collection of nucleic acids on the porous membranes, the membranes may be rotated whilst purification takes place, thus ensuring an even distribution of purified nucleic acids and preventing the build-up of excess nucleic acids at any point (and the loss in efficiency that may accompany such a buildup).

The invention will be further apparent from the following description, with reference to the several figures of the accompanying drawings, which show, by way of example only, one form of purification of nucleic acids. Of the figures.

Experimental

The following experiments detail the purification of DNA from a sample of whole sheep blood with a total process time for purification of about 2 minutes. Gel electrophoresis showed that the DNA collected had not undergone much shearing, a very large proportion of the DNA being at least 23 kb in length. Absorbance spectroscopy shows that at least 60% of DNA available in a sample is collected. PCR testing showed that eluted DNA was functional, being capable of amplification by PCR. Light microscopy showed that the DNA purified by the membrane was substantially free of contaminants such as cellular debris.

Thus the technique exemplified below may be used to rapidly and inexpensively purify nucleic acids from whole cells contained in a sample.

Filter Device

Figure 1:
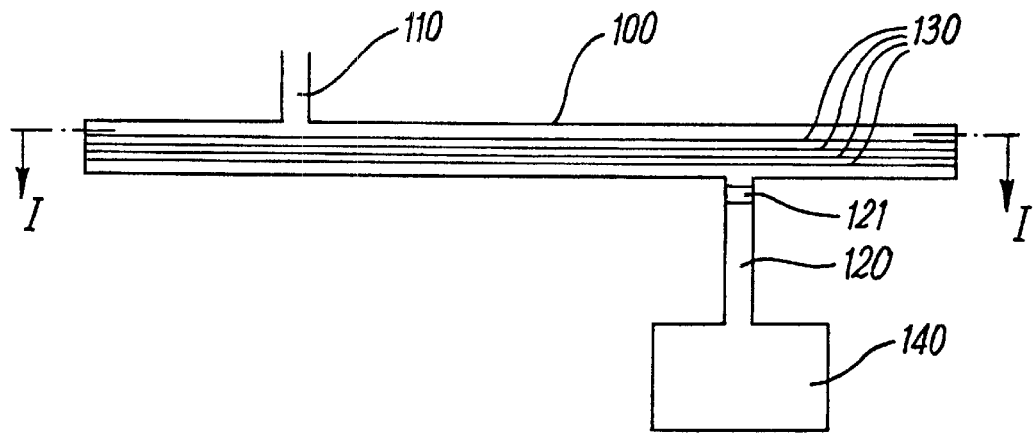
FIGS. 1 and 2 show devices used according to the present invention.

The filter device (FIG. 1) used comprises a main body 100, inlet 110, outlet 120 having 0.5 bar restrictor valve 121 which only opens when pressures of at least 0.5 bar are exerted upon it. Filter membranes 130 comprise 4 hollow polypropylene fibres with pore diameter 0.2 µm and having a total surface area of 6.28 cm². Filtrate passes out of the filter outlet 120 to a collection chamber 140.

Figure 2:
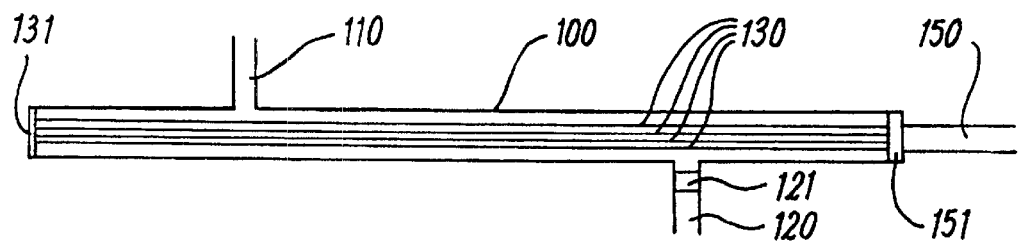

An alternative filter device (FIG. 2) comprises main body 100, inlet 110, outlet 120 having 0.5 bar restrictor valve 121, 4 polypropylene hollow fibre membranes 130 with pore diameter 0.2 µm, sealed at one end 131 and connected to lumen outlet 150 having 0.25 bar restrictor valve 151. Small particles which pass into the lumen of membranes 130 can exit via lumen outlet 150 for e.g. subsequent collection or testing.

Nucleic Acid Purification 5×1 ml of whole sheep blood was passed through a filter device (above). The total time taken to pass the 5 ml of sample through the device was 2 minutes.

Gel Electrophoresis

A 0.8% agarose gel was prepared using 0.8% agarose and 1×TBE buffer (0.8 g agarose/100 ml buffer). Filter membrane from the purification stage was cut up into sections and placed at the top of the gel and one lane filled with molecular weight markers. 125 V was then applied to the gel for 30 minutes. Staining for DNA showed a band at 700 bp and intense staining was observed at the top of the gel where the membrane sections were placed. This indicated that high molecular weight DNA strands may be collected by the membranes.

The experiment was repeated, the gel being run at 125V for 1.5 days and intense staining for DNA was again observed at the top of the gel where the membrane sections were, further suggesting the presence of very high molecular weight DNA strands.

The membranes (carrying the purified DNA) were placed in an eppendorf containing 300 µl water, which in turn was placed in a water bath at 37° C. for 30 minutes to elute the nucleic acids. The solution was then removed and 30 µl 3 M sodium acetate pH 5.4 and 900 µl ethanol added and placed at −80° C. for 5 minutes to preciptate the DNA. The precipitated DNA was then pelletted by spinning at 13,000 rpm for 5 minutes. Supernatant was then removed, the pellet resuspended and the suspension run on a 0.8% agarose gel at 125 V for 1 hour together with molecular weight markers. Visualisation of DNA showed a general smearing at sizes of greater than 23 kb.

DNA Recovery

DNA was eluted from a membrane as above and the mass of recovered DNA calculated using absorbance spectroscopy. This showed that greater than 60% of the total DNA available per ml blood was recovered from the membrane.

PCR Testing

PCR was carried out on both immobilised and eluted genomic DNA collected from 5 ml sheep blood. DNA was purified from the whole sheep blood as above and elution done using water or salt solutions as above. The conditions for PCR were: 1×Taq polymerase buffer, 100 pmole CREb (cyclic adenosine monophosphate response element binding, protein), 0.625 mM $MgCl_2$, 0.25 mM dNTPs, 2.5 U Taq polymerase and genomic DNA template. The reaction mixture was then placed at 94° C. for 5 minutes to denature the DNa, followed by 20 cycles of 2 minutes at 94° C., 2 minutes at 50° C. and 2 minutes at 72° C. The expected product size of CREB is 490 bp. When a sample of the completed PCR reaction was analysed on a 1.2% agarose gel, a 490 bp fragment was seen in both the immobilised and eluted genomic DNA PCR reactions. The negative control which was subject to the same reaction conditions as above but with no template DNA addition showed no PCR product, thus verifying the specificity of the primers and the functionality of the genomic DNA.

Light Microscopic

Figure 3:
FIG. 3 shows a top view through section I–I of FIG. 1.
Figure 4:
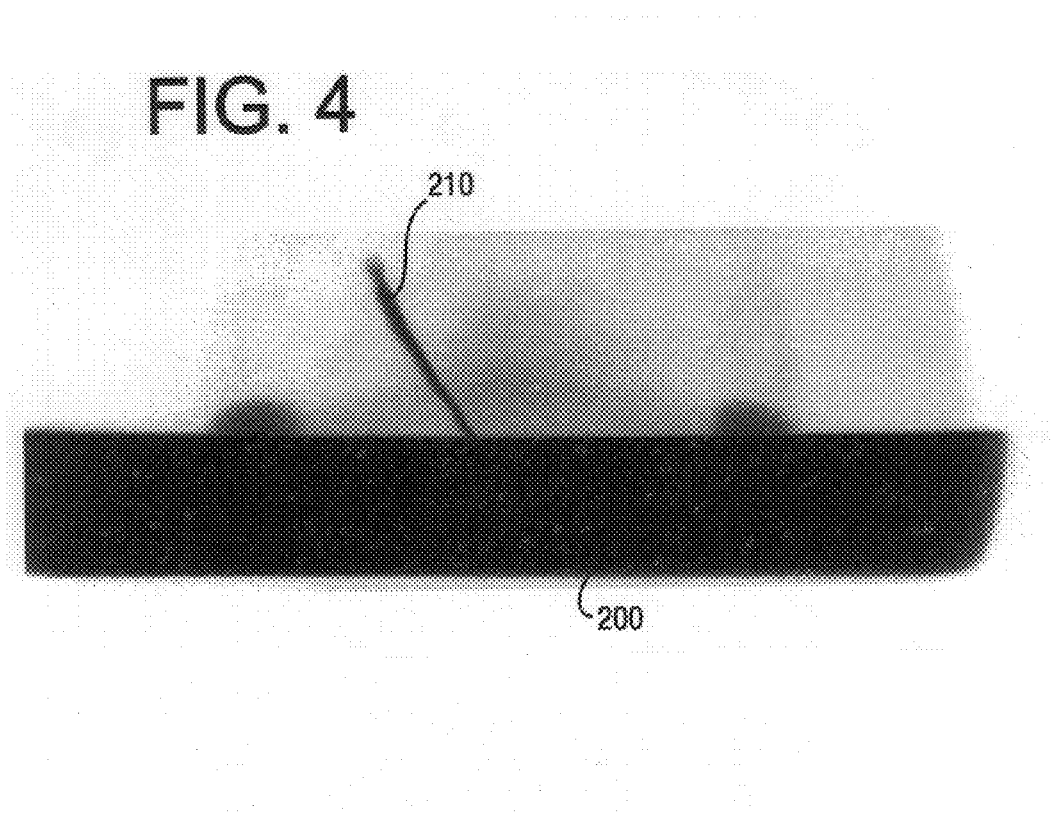
FIGS. 4 and 5 show nucleic acids (10) collected on the surface of a membrane (20).
Figure 5:
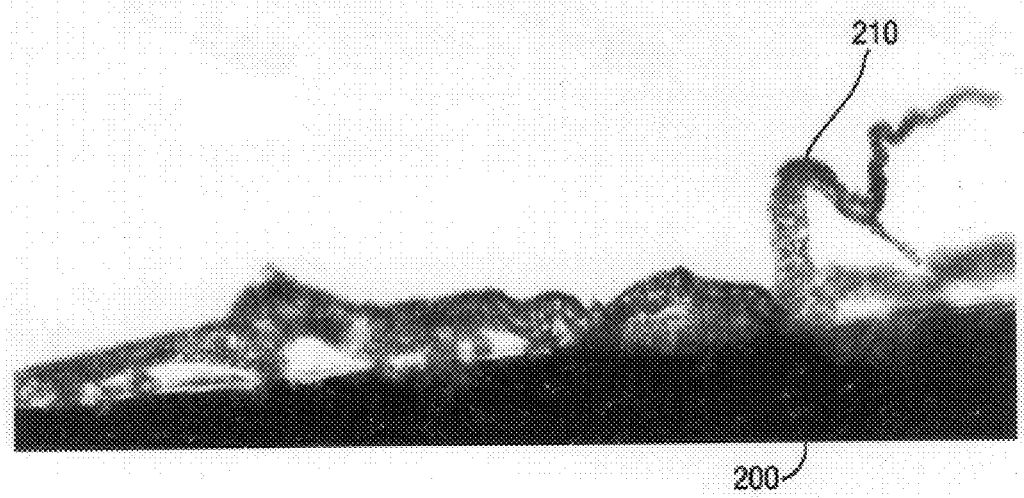

Membranes were removed from filter devices after nuucleic acid purification as above, cut up into sections and placed under a light microscope. Sections are shown at FIGS. 3 and 4, each figure showing about 5 mm of membrane 200, from which can be seen long stretches of DNA 210.

Figure 6:
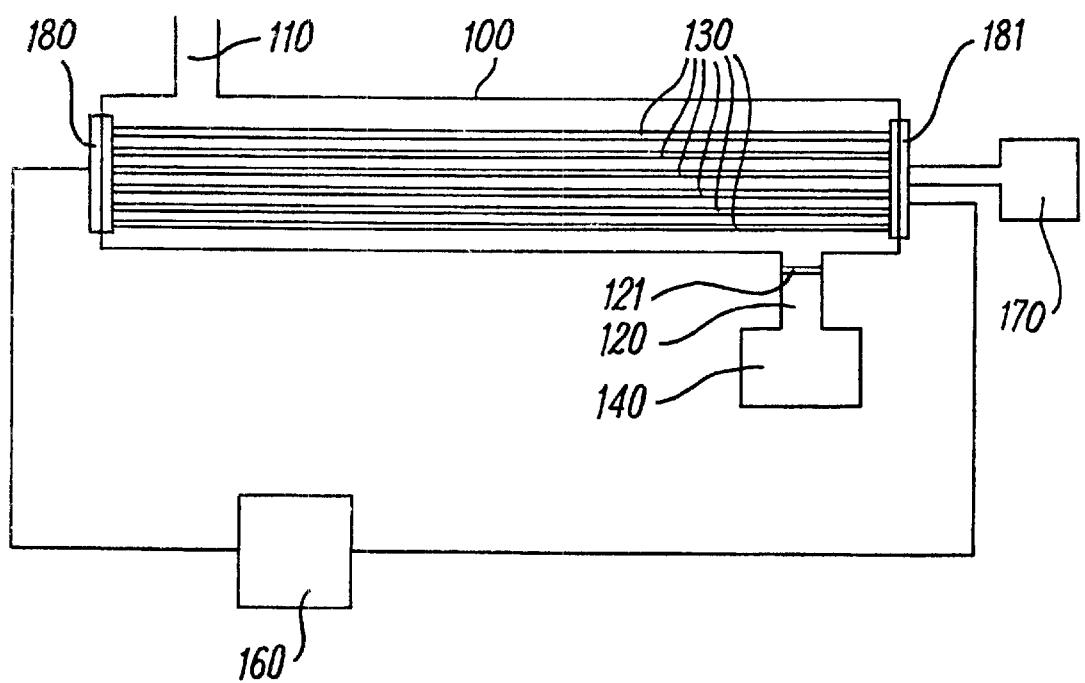
FIG. 6 shows a device for use in the present invention, having means for rotating the membranes and for applying an electrical current along their length.

FIG. 6 shows a filter device comprising main body 100, inlet 110, membranes 130 and outlet 120 having restrictor valve 121 leading to collection chamber 140. Filter membranes 130 are attached to rotatable mountings 180, 181 which are rotated by electric motor 170. Rotatable mountings allow for the rotation of membranes 130 whilst maintaining a water-tight seal and allowing the passage of electrical current provided by signal generator 160, thus allowing the manipulation of nucleic acids on membranes 130.

What is claimed is:

1. A method of purifying nucleic acids from a sample containing, whole cells, comprising the steps of:
   providing a filter device having an inlet and an outlet;
   providing at least one porous membrane contained within the filter device;
   passing the around the porous membrane from the inlet to the outlet; and,
   generating a transmembrane pressure to rupture the whole cells and release the nucleic acids, wherein the nucleic acids are purified from the sample.

2. The method for purifying nucleic acids according to claim 1, the transmembrane pressure being at least 0.25 bar.

3. The method for purifying nucleic acids according to either claim 1, the transmembrane pressure being no greater than 1.25 bar.

4. The method for purifying nucleic acids according to claim 1, the membrane being a hollow fibre membrane.

5. The method for purifying nucleic acids according to claim 4, one end of the hollow fibre membrane being sealed and the other being attached to a lumen restrictor valve.

6. The method for purifying nucleic acids according to claim 1, the nucleic acids comprising DNA and/or RNA.

7. The method for purifying nucleic acids according to claim 1, the membrane occupying at least 50% of the cross-sectional area of the filter device between the inlet and the outlet.

8. The method for purifying nucleic acids according to claim 7, the membrane occupying at least 90% of the cross-sectional area of the filter device between the inlet and the outlet.

9. The method for purifying nucleic acids according to claim 1, comprising the additional step of prefilling the filter device prior to introducing the sample.

10. The method for purifying nucleic acids according to claim 9, comprising an additional flush step after the sample has been introduced into the filter device.

11. The method for purifying nucleic acids according to claim 1, the membrane having pores with a molecular weight cut off of $10^5$–$10^7$ daltons.

12. The method for purifying nucleic acids according to claim 10, the membrane having pores with a molecular weight cut off of about $10^6$ daltons.

13. The method for purifying nucleic acids according to claim 1, the nucleic acids being eluted from the membrane once purified.

14. A filter device comprising:
   a main body;
   a sample inlet and a sample outlet; and,
   at least one porous membrane arranged within the body such that a sample containing whole cells can flow from the inlet to the outlet by flowing around the membrane generating a transmembrane pressure of at least 0.25 bar.

15. The filter device according to claim 14, for use in a method for purifying nucleic acids.

16. A method of purifying nucleic acids from a sample containing whole cells, comprising the steps of:
   providing a filter device having a sample inlet and a sample outlet,
   providing at least one porous membrane within the filter device;
   passing the sample across a surface of the membrane, the sample flowing around the membrane from the inlet to the outlet;
   generating a transmembrane pressure to rupture the whole cells and release the nucleic acids;
   depositing the released nucleic acids oil the surface and interior of the membrane; and,
   eluting the nucleic acids from the membrane.

* * * * *